(12) United States Patent
Ryder et al.

(10) Patent No.: US 6,199,278 B1
(45) Date of Patent: *Mar. 13, 2001

(54) METHOD AND APPARATUS OF INSERTING OCCLUDER(S) IN HEART VALVE PROSTHESES

(75) Inventors: John Kenneth Ryder, Round Rock; Jerry Lee Hodge, Austin, both of TX (US)

(73) Assignee: Sulzer Carbomedics Inc., Austin, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/019,542

(22) Filed: Feb. 6, 1998

(51) Int. Cl.[7] ........................................ B21K 1/24

(52) U.S. Cl. .................. 29/890.124; 29/890.12; 29/283.5; 623/2; 623/901

(58) Field of Search ................ 29/890.124, 890.12, 29/890.13, 283.5; 623/901, 2, 900; 137/512.1

(56) References Cited

U.S. PATENT DOCUMENTS

| | | | |
|---|---|---|---|
| 3,835,475 | * 9/1974 | Child | 137/527.8 |
| 3,903,548 | * 9/1975 | Nakib | 137/512.1 |
| 4,276,658 | * 7/1981 | Hanson et al. | 137/512.1 |
| 5,061,278 | 10/1991 | Bicer . | |
| 5,152,785 | * 10/1992 | Bokros et al. | 137/512.1 |
| 5,336,259 | 8/1994 | Waits et al. . | |

* cited by examiner

*Primary Examiner*—Irene Cuda
*Assistant Examiner*—Trinh Nguyen
(74) *Attorney, Agent, or Firm*—Timothy L. Scott; Philip S. Lyren; Kenneth S. Barrow

(57) ABSTRACT

A method whereby one or more occluders are inserted in the housing of a prosthetic heart valve by compressing the housing of the prosthetic heart valve at four discrete locations, thereby causing the housing to deform sufficiently for insertion of occluders between diametrically opposed pivot supports on the inner surface of the housing. The appropriate locations for application of the compressive forces are identified. Compression force is then applied using either pin blocks or v-shaped blocks. One or more occluders are inserted in the pivot supports. The compressive forces are released, allowing the housing to return to its unstressed generally annular shape and securing the occluders in the housing.

12 Claims, 2 Drawing Sheets

METHOD AND APPARATUS OF INSERTING OCCLUDER(S) IN HEART VALVE PROSTHESES

BACKGROUND OF THE INVENTION

The invention relates generally to prosthetic mechanical heart valves. More particularly, the invention relates to a method and an apparatus for inserting occluders in prosthetic heart valves.

The human heart acts as a pump and includes valves which regulate blood flow in one direction and prevent blood back flow. The heart valves can be damaged or malfunction. A common surgical technique for returning the heart to normal pumping operation is to replace a malfunctioning valve with a prosthetic heart valve. A typical prosthetic heart valve includes an annular housing which defines an orifice for blood flow. The housing supports one or more occluders (also known as leaflets). The occluders open and close in response to changes in blood pressure on either side of the valve, allowing blood flow in one direction. Prosthetic heart valves are manufactured in various sizes to accommodate variations in the size of the heart and valves in different patients.

Prosthetic heart valves are available in several different types. One type of prosthetic heart valve has a single occluder, generally placed off-center so that it pivots in response to changes in blood pressure. Another type of valve, the bi-leaflet valve, includes two occluders or leaflets, each pivotally mounted. A leaflet of a valve typically includes two generally opposed ears or projections which are integral to the leaflet. Each ear fits into corresponding slots or pivot supports on the orifice housing which allows the leaflet to pivot.

The orifice housing of a typical bi-leaflet valve is annular or ring-shaped, and has a generally circular cross-section. The interior surface of the orifice housing has a pair of flat wall sections opposite each other, i.e., diametrically opposed. These flat wall sections are referred to as the orifice flats. The flat surfaces are both secants of the annular shape, cutting off part of the circle on the interior surface of the orifice housing. The result is that this type of valve housing has its shortest interior diameter perpendicular to the orifice flats. Generally, the pivot supports for the leaflets are located within the orifice flats.

One method for installing leaflets in a valve housing is to apply a force to the housing which deforms the housing so that the pivot supports are spread far enough apart to permit the leaflets to be positioned so that the ears align with the pivot supports. When the force is removed, the ears are pivotally mounted in the pivot supports and the housing returns to its annular shape. Valve housings are generally manufactured from materials having sufficient elasticity to allow for some distortion of the housing, e.g., pyrolytic carbon and pyrolytic carbon-coated graphite. After leaflet installation, a stabilizing ring may be shrunk-fit around the exterior surface of the housing to stabilize it and make sure it retains its circular cross-sectional shape.

One technique for installing leaflets in the pivot supports is to engage a set of pins or shoes with the interior surface of the valve housing. The pins or shoes are placed against the housing near the pivot supports. By applying a force to the pins or shoes, the housing is deformed to provide clearance to install the leaflets. After the leaflets are placed into the pivot supports, the force to the pins or shoes is removed and the pins or shoes are retracted.

The insertion of occluders into the valve housing is known as one of the more difficult aspects of designing and manufacturing prosthetic heart valves. The installation of the occluders must meet several requirements. First, the process must provide sufficient occluder capture within the valve housing to prevent leaflet release. If a leaflet comes loose from a prosthetic heart valve after implantation in a patient, the loose leaflet may cause blood vessel embolization, posing a serious health risk for the patient. Therefore, the leaflets must be securely installed in the valve housing and must remain in place, even under high pressures.

Next, the valve housing must be sufficiently stiff to retain the leaflets in place during the pumping operation of the heart. If the housing is too flexible, when the heart flexes during its pumping cycle the leaflets may pop out of the pivot supports.

Another requirement is for the installed leaflets to open and close reliably. If a leaflet sticks, or is jammed open or closed, the result may create a serious health risk for the patient. A stiff valve housing helps to prevent binding between the occluders and the valve housing as the heart flexes, improving reliability.

On the other hand, a stiff valve housing makes leaflet insertion more difficult. The more flexible the housing, the easier it is to deform the housing and move the orifice flats a distance sufficient to allow occluder insertion. However, if the force applied to deform the housing exceeds the fracture stress limitations of the housing material(s), the housing may develop stress fractures or cracks. Generally, valve bodies with cracks must be discarded; therefore, preventing cracks can greatly reduce the expense of valve manufacture. Consequently, the housing must be made from materials which allow these counter-balancing design factors to be met.

As stated above, pyrolytic carbon is a material commonly used for manufacturing the valve housing. The problems of holding the leaflets in place, reliable leaflet opening and closing, and cracking are compounded by certain constraints associated with pyrolytic carbon manufacturing. Two possible approaches for pyrolytic carbon manufacturing are "mandrel" and "substrate" manufacturing. "Mandrel" refers to a core around which the pyrolytic carbon is dip-cast or otherwise shaped. The mandrel is removed after shaping. In substrate manufacturing, the pyrolytic carbon is also shaped around a core, but the core is not removed after shaping.

Mandrel products typically have stress concentration features on the outer surface of the valve housing as a result of coating over pivot detail from the mandrel. Substrate products typically are very stiff due to the greater sectional properties provided by having the substrate present under the pyrolytic carbon coating. These constraints tend to make leaflet insertion more difficult in pyrolytic carbon valves. This is particularly true for the smaller valve sizes, which generally show the greatest stiffness among a family of valve sizes.

Consequently, there is a need for leaflet insertion which maximizes the flat-to-flat deflection of the valve housing within the constraint of its material strength, while not damaging the valve in any way. Such an approach should work for all valve sizes with minimal changes, and work for various valve designs. The method should also be easy to use and reliably repeatable, have little or no dependence on the skill of an operator for success, and be easy to implement in the manufacturing process.

SUMMARY OF THE INVENTION

The present invention is directed to a method and an apparatus for installing occluders in the housing of a prosthetic heart valve. The housing has a generally annular shaped body, with an inner and outer surface. The inner surface has two generally opposed flat surfaces for receiving portions of an occluder. According to the method, a compressive force is applied to the outer surface of the housing at a plurality of discrete points so that the occluder-receiving portions of the housing move a sufficient distance apart to receive the occluder. In one embodiment, the compressive force is applied at four discrete locations on the housing outer surface. The occluder is positioned to align with the receiving portions. The compressive force is removed and the occluder is properly positioned in the housing. The housing returns to its annular shape.

Prior to applying the compressive force, the compressive force required so that the occluder-receiving portions of the housing move a sufficient distance apart to receive the occluder is determined. In one embodiment, this determination is made by directly measuring the displacement of the occluder-receiving portions. In another embodiment, this determination is made using analytical or experimental techniques.

Additionally, the housing is aligned relative to the compressive force so that the compressive force is applied symmetrically to the discrete locations on the outer surface of the housing. Further, the discrete locations for application of compressive force for a given prosthetic heart valve design and prosthetic heart valve size is determined; the locations being selected so that the stress on the housing at a given location is approximately in direct proportion to the strength of the housing at the same location. The stress on the housing and the strength of the housing may be determined by analytical or experimental techniques.

Further, the application of compressive force is limited to the point where the occluder-receiving portions of the housing have moved a sufficient distance apart to receive the occluder.

The apparatus according to the invention includes a support member and a first and second compression member. The first compression member is coupled with the support member. The first compression member includes at least two points for contacting the outer surface of the valve housing. The second compression member is coupled with the support member and is positioned diametrically opposite the first compression member. The second compression member includes at least two points for contacting the outer surface of the valve housing. A compression actuating member is operably coupled with at least the first compression member. The actuating member selectively moves the first and second compression members relative to each other in one dimension.

In one embodiment, the first and second compression members comprise generally v-shaped blocks, each block including a contact surface. The respective contact surfaces are diametrically opposed, and each contact surface has an indentation which is bilaterally symmetrical about a line of symmetry. The indentations are capable of receiving at least a portion of a valve housing and contacting the outer surface of the housing in at least two points. The compression members may be selectively removable. In another embodiment of the invention, the first and second compression members comprise at least two pins extending generally orthogonal to an upper surface of the compression member body.

The first and second compression members may be made from materials including glass, sapphire, ruby, and other materials having a modulus of 200,000 pounds per square inch or greater. In one embodiment, the first compression member is selectively movable relative to the second compression member, and the position of the second compression member is fixed.

A locator is used to align the housing symmetrically with respect to the diametrically opposed compression members with a deviation of 4 degrees or less between a centerline of the housing and the direction of member movement. The compression force is symmetrically applied to the exterior surface of the housing at the desired contact points. The locator may include an angled upper surface which holds one or more occluders in a neutral position during release of a compressive force from the housing. In one embodiment, the locator is positioned between the compression members, and the locator includes stops to halt the compression of the housing when a desired deflection of the housing is achieved. In one embodiment, the locator is capable of translating in one dimension parallel to the compression member movement so as to remain centered between the compression members during compression member movement.

Means are proved for initially positioning a valve housing relative to the compression members.

The present invention provides several advantages. First, a reduction in damage to the valve housing and occluders should be achieved due to the use of four load points and the outer surface of the housing and the optimization of the location of these points. The reduction in damaged valves typically results in lower overall costs. The invention results in a relatively simple product design and a robust process. The method is relatively straightforward for implementation in the factory. For at least some valve designs, a single set of compression members may be used for compression of all valve sizes, without any need to change compression members.

DETAILED DESCRIPTION OF THE EMBODIMENTS

Figure 1:
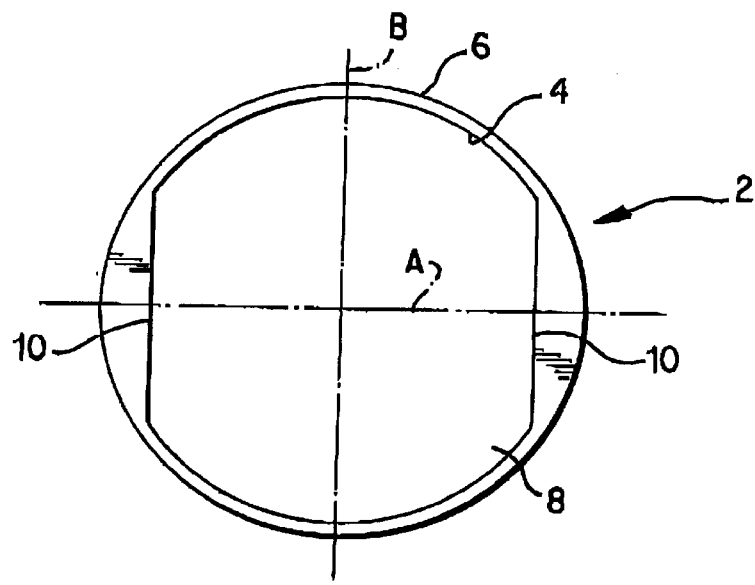
FIG. 1 is a top view of a prosthetic heart valve housing.

The present invention is generally directed to inserting occluders in the housing of a prosthetic heart valve. Referring first to FIG. 1, a prosthetic heart valve housing 2 is generally annular-shaped with an axial length, and includes an inner surface 4 and an outer surface 6. Inner surface 4 defines the limits of valve orifice 8. Inner surface 4 includes generally opposed secants which define generally opposed orifice flats 10. One or more pivot supports (not shown) are positioned on each of the flats 10. Pivot supports receive the ears of one or more occluders. Orifice flats 10 are generally parallel and a line A, extending from flat to flat, defines the shortest inner diameter of housing 2. Centerline B of housing 2 extends perpendicular to line A.

As described in the Background section above, housing 2 must be deformed so that the flat to flat distance is sufficient to allow occluder ears to be positioned in pivot supports. Once occluders are so positioned, the deforming force is relieved so that the housing returns to its generally circular cross-sectional shape. This deformation and release process must be performed without cracking or otherwise damaging housing 2 or occluders. According to the method of the present invention, a compressive force is applied to a plurality of discrete points on outer surface 6 of housing 2 to obtain the desired displacement of pivot supports.

The controlling parameter for occluder insertion is pivot support displacement. In other words, one must determine the amount of compression required to be placed on the plurality of discrete points of the housing outer surface so that the pivot supports are moved sufficiently away from each other to allow the occluder ears to be positioned in the pivot supports. If valve housing 2 were an actual ring, a compressive force applied from a single point on each of two opposite sides in a vertical direction would be expected to produce deflection in a horizontal direction with an expected ratio of vertical to horizontal deflection of 1:1.

However, since actual valve housings have flats, they do not behave in this ideal way. As the size of the valve decreases, the deformation generally becomes more and more non-ideal, with less flat-to-flat deflection for a given arc deflection. Since deflection of an arc generates large tensile stresses on the inner surface under the load point, distributing the load to at least four load points instead of two load points is desirable.

The amount of compression may be determined experimentally by measuring the response of the orifice to an applied load configuration. Compression and load locations can be determined analytically. In another embodiment, the movement of the pivot supports is directly measured. Therefore, the compression force is applied until the pivot supports are sufficiently apart to insert the occluders.

For a particular valve design a minimum of two critical regions are identified. Typically one outer surface and one inner surface of the valve housing are identified as critical. At these regions, the housing strength is measured by standard means, such as stress, deflection or load. Preferably the housing strength is determined by interpretation of housing tension test data. Preferably, the test data is representative of the worst case, or the lowest deflection to failure for a given valve design.

The compression and loading locations may be determined experimentally as explained above, or by means of element analysis or other appropriate techniques simulation analytically. Loading locations for a particular valve design and size are chosen such that the applied stress on the valve housing is in direct proportion to the strength of the housing in a given location. The stress on the housing may include the residual effects of the manufacturing process as appropriate. The flat-to-flat deflection of the housing to be expected for a given compressive force at four locations can also be determined by analytical or experimental techniques.

Once the loading locations are determined, the housing must be positioned in a neutral initial position. Various methods, described further below, may be used. The leaflets must be positioned in a neutral position with respect to the pivot supports on the housing. In one embodiment, a locator feature is used. Additionally, compression stops are determined to prevent the housing from being over-stressed. This feature may be incorporated with the locator.

The compression force is then applied to the plurality of discrete points. The housing is compressed until sufficient pivot support separation is reached. The leaflets are then positioned to fit in the pivot supports. The compression force is then relieved, allowing the valve housing to return to approximately its original annular shape. By properly applying the load at the discrete points, the housing should not be cracked or otherwise damaged. Also, the leaflets should be positioned to function properly.

Figure 2:
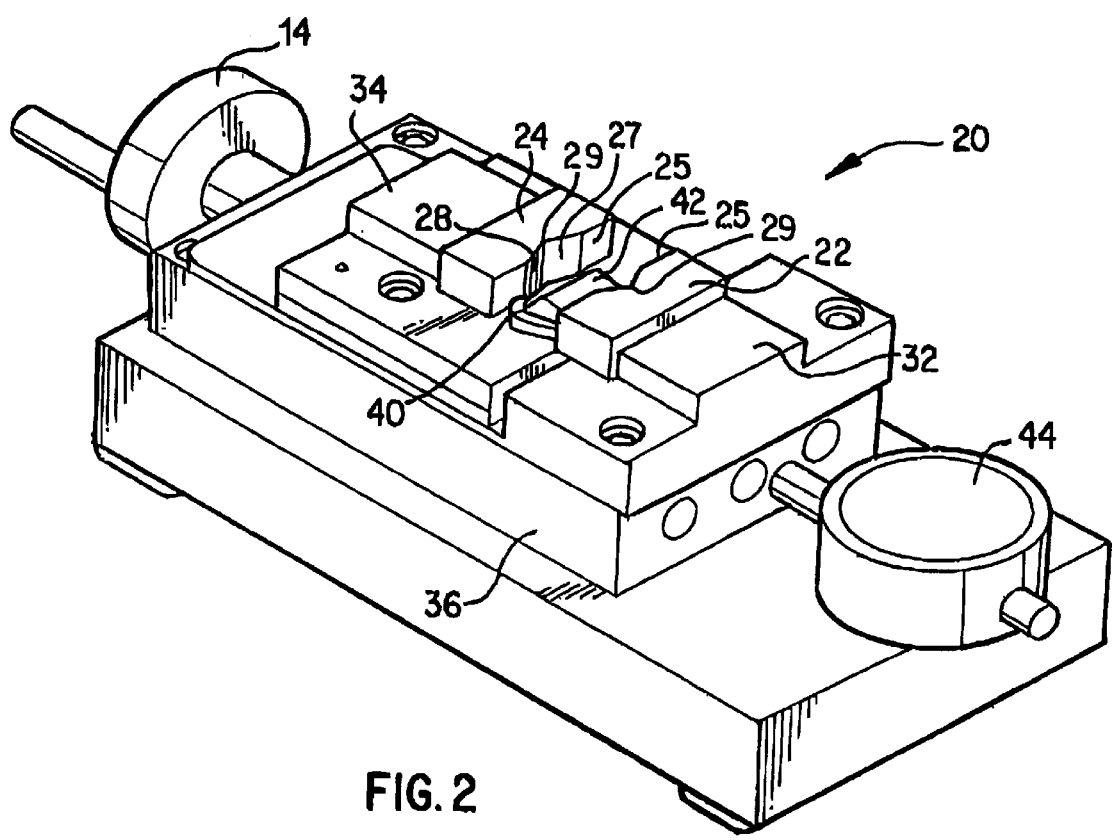
FIG. 2 is a perspective view of an apparatus for compressing a valve housing.

FIG. 2 is a perspective view of an apparatus 20 for compressing an orifice housing of a prosthetic heart valve in order to insert one or more occluders. An orifice housing (not shown) is positioned between diametrically opposed compression members 22, 24. The valve-contact sides of members 22, 24 each have an indentation 29 defined by contact surface 25 which is bilaterally symmetrical about a line of symmetry. The indentation 29 of compression members 22, 24 has two sides 27, 28, one on each side of the line of symmetry 26. Housing 2 will contact each side 27, 28 in at least one location. Compression members 22, 24 may be sized to accommodate one particular valve housing size, or a range of valve sizes, or for all valve sizes for a given valve design.

The compression member indentations may be of various shapes. In one embodiment, surfaces 25 are linear, so that sides 27, 28 of the indentations are planar (as shown in FIG. 2). For at least some heart valve designs, the planar configuration allows for the use of the same set of compression members 22, 24 for compression of several different sizes of valves. The depth of the indentations and the angle between sides 27, 28 may vary for different valve designs and valve sizes. The optimal angle is determined by the strength and the specific geometry of housing 2, as described above. Preferably housing 2 should be stressed in a manner which is in a 1:1 ratio with the strength of housing 2. This maximizes the deformation of housing 2 prior to failure. For example, if the loading points have an angular separation of 40 degrees, an angle of 140 degrees would be required between sides 27, 28.

In other embodiments of the invention, other geometries for the indentations are possible. A higher order curve may be constructed to define sides 27, 28. Such a compression member may be used in the same fixture as compression members having other geometries. Also, sides 27, 28 may have parabolic surfaces or other smooth curves with faces parallel to the exterior surface of housing 2. The curve is preferably selected so that the same set of compression members can be used for all different sizes of valves of a given valve design. Parabolic or spline edge geometry is constructed by appropriate regression to the optimum load region centers for each valve orifice housing size. For either flat or curved indentation surfaces, the maximum deformed shape for a given range of valve sizes should be checked for fit into the compression members.

Compression members 22, 24 may be constructed from any number of materials of sufficient stiffness to provide an optimum stress proportion. Materials for compression members 22, 24 should also be sufficiently stiff to resist permanent deformation of sides 27, 28 while in service. Use of such stiff materials avoids problems with irregularities in sides 27, 28 developing from repeated use. Stiffer valve designs may require stiffer materials to carry the greater loads during insertion of the leaflets.

The compression member materials will preferably have stiffness greater than 200,000 pounds per square inch (psi). Modulus is a measure of stiffness; a material with a high modulus is very stiff. For pyrolytic carbon valve housings in particular, the compression materials must have a modulus greater than 200,000 psi. Materials such as glass, sapphire, and ruby, which have a high modulus, are suitable.

Sides 27, 28 must be polished or finished to a level which will permit rotation of the orifice housing. The compression member material is preferably able to receive a standard surface finish or polish of 63 RMS or better, and should be finished to grade 63 RMS or better. The height of sides 27, 28 should be sufficient to direct the compression of the housing to within 5% of the target compression for a selected load configuration.

The side opposite the valve-contact side on compression member 22 is in contact with support member 32, and the side opposite the valve-contact side on compression member 24 is in contact with support member 34. Support members 32, 34 are centered with respect to one another. Compression members 22, 24 are mounted on support members 32, 34, respectively. Compression member 22 and support member 32 are fixedly mounted on fixture 36, while compression member 24 and support member 34 are mounted to be selectively movable toward or away from compression member 22/support member 32.

A compression actuating member, such as a screw mechanism 14 or other suitable actuating mechanism, causes controlled movement of compression member 24/support member 34 in the desired direction.

When a housing 2 is positioned between compression members 22, 24, the compression members may be centered with respect to the height (i.e., axial length) of housing 2. If so, the compression members preferably cover at least 25% of the housing height. The compression members may also rest on the same base surface on which housing 2 rests. If so, the compression members should preferably cover at least 60% of the housing height. If the compression members are not centered with respect to the housing height and also do not rest on the same base surface as the housing, the compression members should preferably cover at least 60% of the height of housing 2.

This coverage by the compression members is sufficient to prevent housing 2 from slipping from between the compression members during compression. Most preferably the height of the compression members is somewhat higher than the height of housing 2, to provide a margin for error. In one embodiment, the height of the compression members is approximately 105–110% of the housing height.

Compression members 22, 24 and/or support members 32, 34 may be either permanently attached to fixture 36 or interchangeable. Preferably a single fixture 36 is used for all valve sizes of a given design. Fixture 36 provides sufficient rigidity to prevent the compression member surfaces from becoming unparallel to each other or to the outer surface of the orifice housing. As typically the smallest valve size of a given design has the greatest stiffness, if the rigidity of fixture 36 is sufficient for the smallest size, generally it is sufficient for all other sizes.

A locator 40 is positioned between compression members 22, 24 and enables an operator to align housing 2 properly between compression members 22, 24. Proper alignment assures that housing 2 will contact compression members 22, 24 at the correct four locations for compression. The load points must be approximately symmetric about the centerline B of the orifice housing 2. The alignment of the centerline B of the orifice housing 2 with respect to compression members 22, 24 preferably is controlled to within 1–2 degrees during compression.

Locator 40 generally controls the alignment of housing 2 with respect to compression members 22, 24. Locator 40 minimizes the chance of asymmetric loading and simplifies the installation of the leaflets. In one embodiment, locator 40 serves an additional purpose of aiding in proper leaflet placement with respect to pivot supports 12, making the process more robust. Locator 40 preferably has two angled upper surfaces 42 for leaflet positioning. For a bi-leaflet valve, upper surfaces 42 are used to place both leaflets in a neutral position while housing 2 is compressed. This neutral position helps to ensure that the leaflets do not slip out of pivot supports as the compressive forces are relaxed and housing 2 returns to its unstressed configuration. In another embodiment, a single upper surface is used to place a single leaflet in a neutral position during insertion into a single leaflet valve.

Locator 40 preferably is also designed to stop the compression of housing 2 when housing 2 has deflected the proper amount or when the proper compressive force has been applied. Stops can be integrated with the locator, or placed on the fixture between the blocks, or in any manner that would stop the blocks from moving toward one another once the desired deformation is achieved which prevents an operator from accidentally overloading and perhaps damaging housing 2. The stops also simplify the operation of the apparatus. If locator 40 is used to stop deflection, the locator is preferably made of a material having a stiffness of at least 100,000 psi. This stiffness value provides sufficient resistance to the compression forces for sensing the stops by manual or automated means. Otherwise, locator 40 may be made of any material which is dimensionally stable enough so that it does not bend or change size when in service. Locator 40 may also have indicators to show the extent of displacement incorporated into it. Locator 40 may have any suitable surface finish.

Locator 40 preferably is capable of sliding or otherwise translating relative to compression members 22, 24 as movable compression member 24 moves toward or away from stationary compression member 22. This translation allows locator 40 to remain centered with respect to the pivot features of housing 2 and to stop the deflection symmetrically, even though only one of the compression members is moving. In one embodiment, locator 40 fits in a slot (not shown) to provide the sliding capability.

A load measurement device 44 attached to fixture 36 measures the load on housing 2. This allows for accurate determination of the initial position for a particular housing and also prevents overloading. Determination of the starting point or initial position is important because this may be the difference between success and failure of occluder insertion in some valves. However, an exact determination of the initial position is less important with the present invention than with some other processes, as the housing is stressed in direct proportion to its strength in critical regions. The initial position may be set by several methods, including manual means, by means of a load transducer, by electrical circuit, or by displacement indicators.

Initial position of compression members 22, 24 may be set manually by manual manipulation of housing 2 between members 22, 24. Compression members 22, 24 assist in manual zeroing because they allow for manual manipulation of housing 2 during the zeroing process. Locator 40 provides for re-alignment if necessary. Repeatability of the zeroing process may be assured through training.

One technique for confirming a correct initial position of compression members 22, 24 is to lift housing 2 slightly from the base surface on which it rests between compression members 22, 24. If housing 2 slips back easily into place with only the force of gravity, the initial position is incorrect in that it is too loose. If considerable force is required to push housing 2 down into place, the initial position is too tight. If only a minimal amount of force is required in addition to gravity, then the initial position is correct.

Initial positioning of compression members 22, 24 also may be set by placing a load transducer in line with support members 32, 34, and in line with housing 2. The compression members are at "zero" once the specified load reading is achieved. A load cell may be incorporated into the load train and utilized by the operator to zero the load by moving movable compression member 24.

Initial positioning of compression members 22, 24 also may be set by an electrical circuit. Assuming housing 2 and compression members 22 24 are made of suitably conducting materials, an air gap between housing 2 and compression members 22, 24 provides an essentially infinite resistance, so that no current will flow when there is a gap. The circuit will be completed when at least two of the four loading locations on housing 2 are in contact with compression members 22, 24. Geometric tolerancing should insure the remaining gaps are sufficiently closed for successful operation. A completed circuit indicates a correct initial position.

Optical methods for establishing zero may be used by incorporating transparent or semitransparent compression members and light sources into fixture 36. An optical interference technique can be used to determine contact between compression members 22, 24 and housing 2. Contact indicates a correct initial position.

Displacement indicators can be placed on or within fixture 36 and registered in some manner to the blocks; the indicators may be used to set both initial position and to measure the extent of deflection during compression. Displacement indicators may be used to indicate how far housing 2 has been deflected inward under the loading points, or outward at the pivot supports. The distance housing 2 must be deflected inward under the loading points for a desired outward deflection can be determined analytically or experimentally. Measuring the extent of outward deflection at the pivot supports has the advantage of being direct, since the purpose of the compression is to provide sufficient clearance for leaflet installation.

For either type of measurement, the deflection indicators are preferably mounted so that they can slide relative to compression members 22, 24 as movable compression member 24 moves toward or away from stationary compression member 22. This sliding ability allows the displacement indicators to remain centered with respect to the pivot features of housing 2 and with respect to compression members 22, 24, even though only one of the compression members is moving. The displacement indicators preferably are incorporated into locator 40.

Figure 3:
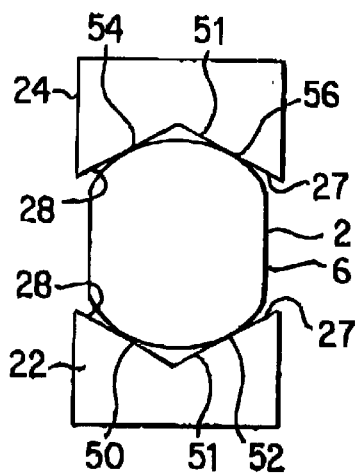
FIG. 3 is a partial top view of the compression members of FIG. 2.

FIG. 3 is a partial top view of compression members 22, 24 and housing 2. The sides 27, 28 of the indentations in each of the compression members contact outer surface 6 of housing 2. The sides 27, 28 of the compression members show local geometric tangency to outer surface 6 of housing 2 at compression contact surfaces 50, 52, 54, and 56. Each compression contact surface contacts one of the four discrete locations for application of compressive forces to outer surface 6 of housing 2 by movement of movable compression member 24. Each compression member applies compressive force to outer surface 6 housing 2 to distend the housing as movable compression member 24 moves toward stationary compression member 22.

Figure 4:
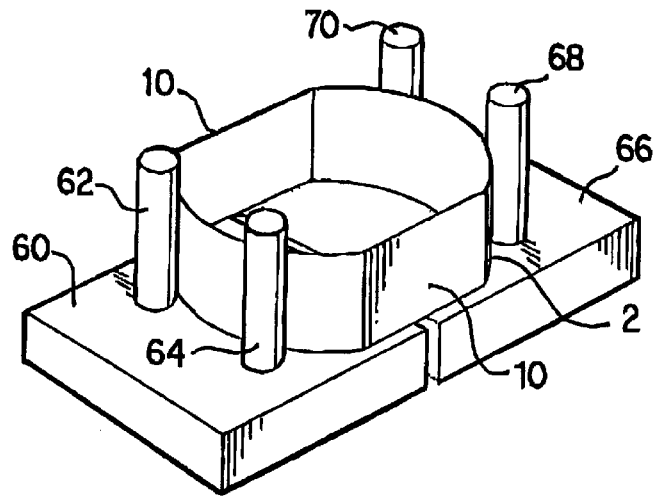
FIG. 4 is a perspective view of a set of pin blocks and a valve housing.

FIG. 4 is a perspective view of another embodiment of the invention. In this embodiment, the v-shaped blocks of FIG. 2 are replaced by pin blocks. Stationary pin block 60 has two pins 62, 64 extending orthogonally from it. Movable pin block 66 has two pins 68, 70 extending orthogonally from it. Each of the pins 62, 64, 68, 70 has the shape of a right circular cylinder. Movable pin block 66 is mounted on a fixture (not shown) so as to be capable of one-dimensional movement toward and away from stationary block 60. The pins may be arranged to accommodate one particular orifice housing size, or a range of valve sizes, or for all valve sizes for a given valve design. Pin blocks 60, 66 may be interchangeable so that several different types or sizes may be used in the same fixture, or each pin block may be permanently attached to a fixture. The pins may be removably attached to the pin block. Several pin attachment locations may be available for attaching pins to a pin block.

The height of the pins should preferably be at least 60% of the height of housing 2. This pin height is sufficient to prevent housing 2 from slipping off the pins during compression. Preferably the height of the pins is somewhat higher than the height of housing 2, to provide a margin for error. In one embodiment, the height of the pins is approximately 105–110% of the housing height.

The pins may be made of any of a variety of materials having sufficient stiffness to provide an optimum stress proportion. The stress preferably is in a 1:1 ratio with the local orifice housing strength, which maximizes the deformation of housing 2 prior to failure. The pin stiffness should be sufficient so that repeated compressions of housings do not damage the pins. The pin diameter should be large enough to minimize bending of the pins on contact with housing 2 and to optimize contact with the deformed shape of the housing.

The material selected for the pins also affects the required pin diameter. The pin surfaces should be polished or finished to a level which will permit rotation of housing 2. Precise knowledge of the deformed shape of the housing is not necessary for compression with pin blocks. The pin blocks 60, 66 may be mounted in any suitable fixture, including one similar to fixture 36 shown in FIG. 2.

Figure 5:
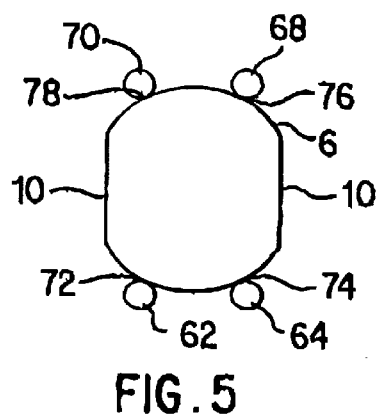
FIG. 5 is a partial top view of the set of pin blocks of FIG. 4.

FIG. 5 is a partial top view of the set of pin blocks of FIG. 4, showing the pins 62, 64, 68, 70 and housing 2. The pins contact outer surface 6 of housing 2 on pin contact surfaces 72, 74, 76, 78. The surfaces of the four pins show local geometric tangency to outer surface 6 of housing 2 at the four pin contact surfaces 72, 74, 76, 78. Each pin contact surface contacts one of the four discrete locations on outer surface 6 of housing 2 for application of compressive forces by movement of movable pin block 66. Each pin applies compressive force to outer surface 6 of housing 2 to deform housing 2 as movable pin block 66 moves toward stationary pin block 60.

Figure 6:
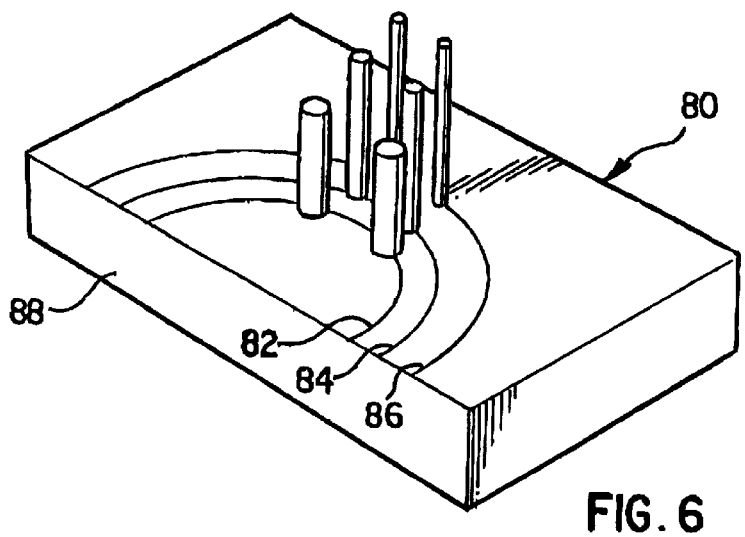
FIG. 6 is a perspective view of a single pin block with three pairs of pins.

FIG. 6 is a perspective view of a single pin block 80 with three pairs of pins, in accordance with another embodiment of the present invention. Locations for pin installation are at three different distances, 82, 84, and 86, from the contact side 88 of the pin block. Each pair of pins has a different diameter and height. Any of the pairs of pins may be installed at distances 82, 84, or 86 from the contact side of the pin block. This arrangement permits a great deal of flexibility in the locations of the pins so as to easily accommodate a variety of heart valve designs and valve sizes. The pin block 80 may be mounted in any suitable fixture.

Small size valves (generally less than 24 mm in diameter) are the most difficult valves to manufacture as they are most likely to be damaged during leaflet insertion. During the compression of a small size valve by opposing forces, the housing often fails from the interior surface under one of the load points. Distributing the load lowers the stresses under each load point. Compression at two load points on each side of the orifice housing provides adequate load distribution. Typically, the housing strength is determined by interpretation of housing tension test data. The housings tested are part of a lot of valves known to have a low deflection to failure, so that the worst case is represented. Based on the results for housing strength, in one embodiment of the invention optimum loading locations are at approximately 20 degrees to each side of centerline B of housing 2. A pair of loading locations is located on each of the diametrically opposed sides of housing 2. Consequently, an angular separation of about 40 degrees between each pair of loading locations on each side of the valve is used. The optimal angle between the loading points remains the same for all valve sizes.

Other embodiments are within the scope of the following claims.

We claim:

1. A method of inserting one or more occluders in a prosthetic heart valve housing, the housing comprising a generally annular body having an inner and an outer surface, the inner surface including generally opposed surfaces for receiving generally opposed portions of the occluder along a line connecting said opposed surfaces, the method comprising:

applying compressive force in a direction perpendicular to said line connecting said opposed surfaces at four discrete locations on the housing outer surface through at least two compressive members, each compressive member having local geometric tangency where said compressive member contacts said heart valve housing, a first two of said four locations being on a first side of said line connecting said opposed surfaces and a second two of said four locations being on a second side of said line, said first two locations being separated by an angle of no more than 40° and said second two locations being separated by an angle of no more than 40° so that the opposed surfaces of the housing move a sufficient distance apart to receive the occluder;

positioning the occluder to align with the occluder-receiving opposed surfaces of the housing inner surface; and removing the compressive force.

2. The method of claim 1, further comprising the step of determining the compressive force required so that the occluder-receiving portions of the housing move a sufficient distance apart to receive the occluder.

3. The method of claim 2, wherein the step of determining the compressive force required is made by directly measuring the displacement of the occluder-receiving portions.

4. The method of claim 2, wherein the step of determining the compressive force required is de termined from analytical techniques.

5. The method of claim 1, further comprising the step of aligning the housing relative to the compressive force so that the compressive force is applied symmetrically to the discrete locations on the outer surface of the housing.

6. The method of claim 1, further comprising the step of determining said at least four discrete locations for application of compressive forces for a given prosthetic heart valve design and prosthetic heart valve size, the locations being selected so that the stress on the housing at a given location is in proportion to the strength of the housing at the same location, wherein the stress on the housing and the strength of the housing being determined by analytical techniques.

7. The method of claim 1, wherein the four locations for application of compressive forces to the housing outer surface are located at angles of 20 degrees, 160 degrees, 200 degrees, and 340 degrees from a centerline of the housing.

8. The method of claim 1, further comprising the step of limiting the application of compressive force when the occluder-receiving portions of the housing have moved a sufficient distance apart to receive the occluder.

9. The method of claim 1 wherein said compressive members are made from a material selected from the group consisting of glass, sapphire, or ruby.

10. The method of claim 1 wherein said compressive force is applied at each of said discrete locations through compressive members maintaining line contact with said heart valve housing.

11. The method of claim 2, wherein the step of determining the compressive force required is determined from experimental techniques.

12. The method of claim 1, further comprising the step of determining said at least four discrete locations for application of compressive forces for a given prosthetic heart valve design and prosthetic heart valve size, the locations being selected so that the stress on the housing at a given location is in proportion to the strength of the housing at the same location, wherein the stress on the housing and the strength of the housing is determined by experimental techniques.

* * * * *